US011224486B2

(12) United States Patent
Barral et al.

(10) Patent No.: US 11,224,486 B2
(45) Date of Patent: Jan. 18, 2022

(54) GLOBAL SYNCHRONIZATION OF USER PREFERENCES

(71) Applicant: Verily Life Sciences LLC, Mountain View, CA (US)

(72) Inventors: Joëlle K. Barral, Mountain View, CA (US); Martin Habbecke, Palo Alto, CA (US); James Shuma, San Jose, CA (US); Robin Thellend, Sunnyvale, CA (US); Miles Eldon, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 648 days.

(21) Appl. No.: 16/108,926

(22) Filed: Aug. 22, 2018

(65) Prior Publication Data

US 2020/0060773 A1  Feb. 27, 2020

(51) Int. Cl.
*G05B 19/04* (2006.01)
*A61B 34/00* (2016.01)
(Continued)

(52) U.S. Cl.
CPC ............ *A61B 34/25* (2016.02); *G05B 13/027* (2013.01); *G06F 1/12* (2013.01); *G06F 9/4451* (2013.01); *G06F 9/451* (2018.02); *A61B 34/35* (2016.02); *A61B 2034/256* (2016.02); *A61B 2034/258* (2016.02)

(58) Field of Classification Search
CPC ........ A61B 2034/256; A61B 2034/258; A61B 34/25; A61B 34/35; G05B 13/027; G05B 19/409; G05B 2219/24162; G05B 2219/36542; G06F 1/12; G06F 9/4451; G06F 9/451
See application file for complete search history.

(56) References Cited

U.S. PATENT DOCUMENTS 8,418,073 B2    4/2013  Mohr et al.
9,258,415 B1 *  2/2016  Walton .................. G06F 16/215
(Continued)

OTHER PUBLICATIONS

International Search Report & Written Opinion for corresponding International Patent Application No. PCT/US2019/047503, dated Nov. 27, 2019, 15 pages.
(Continued)

*Primary Examiner* — Harry Y Oh
(74) *Attorney, Agent, or Firm* — Christensen O'Connor Johnson Kindness PLLC

(57) ABSTRACT

A robotic system includes a communication system coupled to communicate with one or more external devices that include first user preferences. The robotic system also includes memory storing a database including second user preferences. A controller is coupled to the user interface, the communication system, and the memory, and the controller includes logic that when executed by the controller causes the robotic system to perform operations. Operations may include retrieving the first user preferences using the communication system; retrieving the second user preferences from the database; resolving conflicts between the first user preferences and the second user preferences to create a final set of user preferences; and configuring the robotic system with the revised set of user preferences.

22 Claims, 6 Drawing Sheets

(51) Int. Cl.
*G06F 9/451* (2018.01)
*G05B 13/02* (2006.01)
*G06F 1/12* (2006.01)
*G06F 9/445* (2018.01)
*A61B 34/35* (2016.01)

(56) References Cited

U.S. PATENT DOCUMENTS

| | | | | |
|---|---|---|---|---|
| 2006/0149418 | A1* | 7/2006 | Anvari | A61G 13/10 |
| | | | | 700/245 |
| 2010/0228264 | A1* | 9/2010 | Robinson | A61B 34/35 |
| | | | | 606/130 |
| 2010/0274386 | A1* | 10/2010 | Chang | B25J 9/1656 |
| | | | | 700/245 |
| 2012/0110125 | A1* | 5/2012 | Chen | G06F 40/117 |
| | | | | 709/218 |
| 2012/0254108 | A1* | 10/2012 | Wedewer | H04W 4/60 |
| | | | | 707/618 |
| 2014/0033123 | A1* | 1/2014 | Hockmann | G06F 8/65 |
| | | | | 715/810 |
| 2014/0052343 | A1* | 2/2014 | Chen | B60N 2/002 |
| | | | | 701/49 |
| 2014/0267658 | A1 | 9/2014 | Speier et al. | |
| 2015/0223897 | A1 | 8/2015 | Kostrzewski et al. | |
| 2016/0000517 | A1* | 1/2016 | Kehat | G06F 3/14 |
| | | | | 600/424 |
| 2016/0001411 | A1* | 1/2016 | Alberti | G05B 19/402 |
| | | | | 700/188 |
| 2016/0006804 | A1 | 1/2016 | Deshpande et al. | |
| 2016/0375306 | A1 | 12/2016 | Gu et al. | |
| 2017/0135587 | A1 | 5/2017 | Desroches | |
| 2018/0078034 | A1* | 3/2018 | Savall | B25J 13/088 |
| 2019/0166343 | A1* | 5/2019 | Anders | G02B 27/0172 |
| 2019/0254763 | A1* | 8/2019 | Lambrecht | A61B 34/35 |
| 2020/0389804 | A1* | 12/2020 | Sharma | H04W 76/11 |

OTHER PUBLICATIONS

"Syncbase for Android," Syncbase for Android—Vanadium, Syncbase, https://vanadium.github.io/syncbase/, accessed Aug. 22, 2018, 2 pages.

* cited by examiner

GLOBAL SYNCHRONIZATION OF USER PREFERENCES

TECHNICAL FIELD

This disclosure relates generally to robotic systems.

BACKGROUND INFORMATION

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of surgery, robotically controlled instruments may replace traditional tools to perform surgical motions. Feedback-controlled motions may allow for smoother surgical steps than those performed by humans. For example, using a surgical robot for a step such as rib spreading may result in less damage to the patient's tissue than if the step were performed by a surgeon's hand. Additionally, surgical robots can reduce the amount of time a patient spends in recovery by facilitating smaller incisions.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1A:
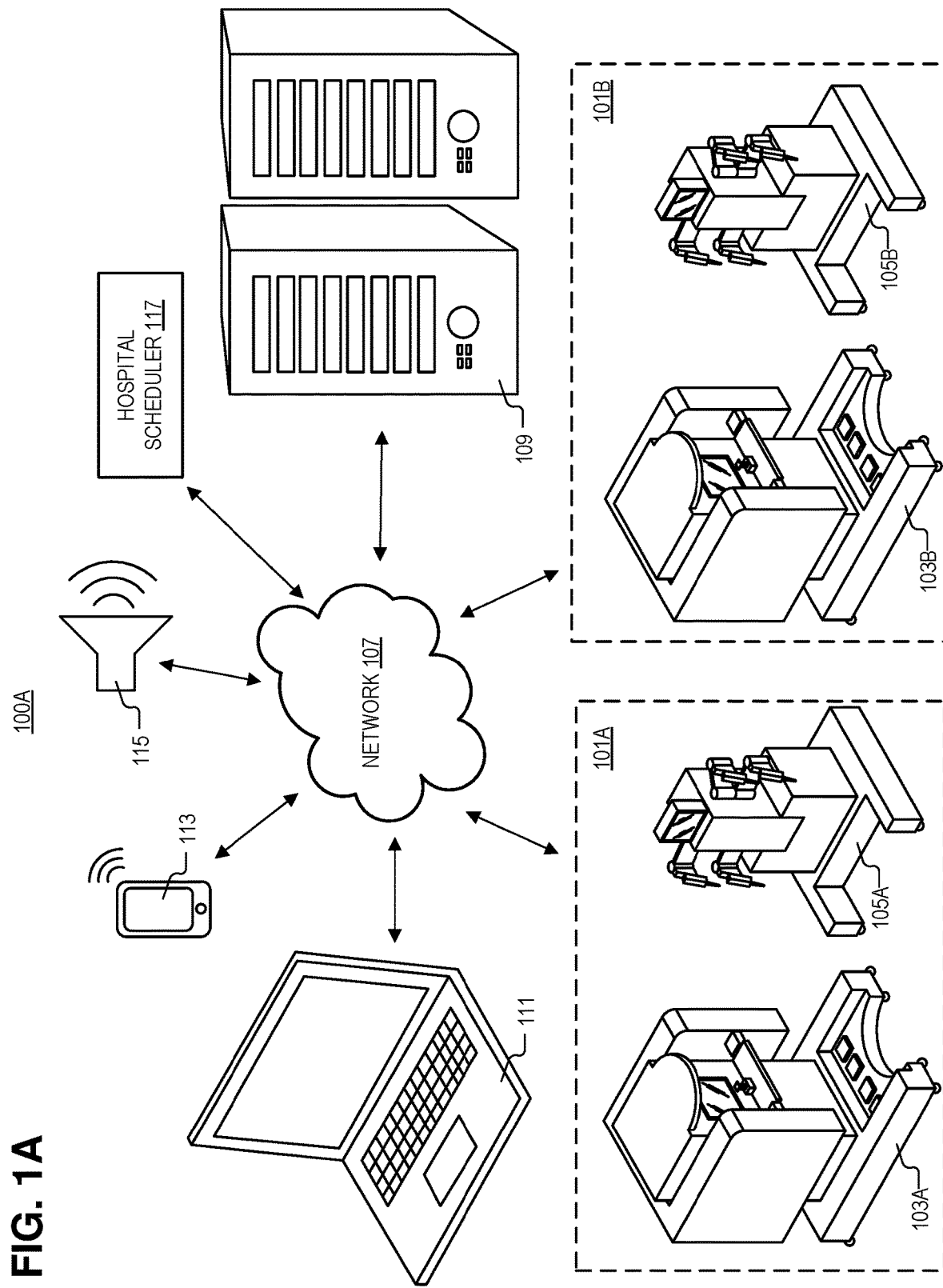
FIG. 1A illustrates a system for global synchronization of surgical robots, in accordance with an embodiment of the disclosure.

Embodiments of a system and method for global synchronization of user preferences are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Most surgeons operate in more than one hospital. Today, if surgeons perform robotic cases, it means that they have to adjust robot preferences for each of the robots they use, independently. Adjusting preferences takes time, typically when a patient is already under anesthesia, and it adds imprecision to the surgery since it is impossible for the surgeon to perfectly tune (manually) each robot so that the surgeon's experience is the exact same across many institutions. Ideally, surgeons would like to have their personal preferences and settings replicated globally, automatically: the user experience should be identical across all systems in the world, and the system should adopt user settings stored in the robot and on the cloud automatically with limited or no human involvement.

Doing this is complicated by the fact that network connectivity may be intermittent, unreliable, or totally absent. Additionally, in the event of conflicts, it is necessary to resolve the conflicts such that the latest change (or change with greater weight in a hierarchy) wins, irrespective of the order in which systems connect to the network. Given the critical nature of the system's work, the system should operate without a user ever having to administer it, either to perform a synchronization or to resolve conflicts. Moreover, it is important to minimize bandwidth utilization. The system must also prevent a user from having access to another user's data, and the system must prevent an app from reading another app's data, even from the same user, unless explicitly allowed to do so.

The system described here may include the following components: a SQL-based database (or other database or key-value store) inside the surgical robot; a server process inside the robot that allows client applications inside the robot to programmatically interact with the database by remote procedure call (RPC); client applications inside the robot that interact with the server process, and also interact with the user via a graphical user interface (GUI); a background service that syncs the preference database with a remote endpoint (this remote endpoint is either the web portal or a connectivity hub that proxies this connection); as an alternative for systems that are not provided with network connectivity, the system may include logic to read externally generated updates from removable media that have been retrieved from the web portal, and writable internally generated updates to removable media that can be uploaded to the Web Portal; a service running inside the robot that synchronizes the robot's clock with a central time authority; a service running in the cloud that receives sync data over the network; a user interface for downloading updates addressed to a robot, and receiving updates from a robot (this is provided as a way to interface with the alternative sync mechanism that is provided to robots lacking network connectivity); and a database that stores data, residing in the Cloud.

In some embodiments, on the robot as well as in the cloud, each user preference entry in the relevant database is structured as: the user that the preference applies to; the key identifying the preference—this is structured as an app ID and a related application-visible key (e.g., com.verily.ergonomics.chair.lumbarheight); the value of the preference, stored as a string (in some embodiments, a machine learning algorithm may be applied to set sensible defaults based on information the system collects about the user, such as locale and biometric data); the timestamp that this setting was made; and a flag indicating whether this entry exists (this defaults to true, but is set to false when a deletion happens). Here if the system handled deletions by just dropping the entry from the database, this may not percolate deletions elsewhere, and later syncs might end up re-creating it. However, by having a separate existence field in the database, the system can treat existence as a piece of data that can be updated, and which may override older versions of that existence status.

The robot's clock and the cloud service's clock are always kept in sync, so that timestamps are relative to the same time authority. The sync service running on the robot maintains a record of the timestamp of the last successful sync.

In some embodiments, when the sync service on the robot connects with the cloud over the network, it requests all updates that were made after the last successful sync; it applies only the entries that are newer than what is present on the robot, or which are not present on the robot; and it conveys all changes that have a timestamp newer than the last successful sync (not including those that were downloaded in the current sync session) to the cloud. All entries are required to be independently updatable. If there are edits that must be made atomically or must be kept in sync, the client must structure its data such that all such tied data is kept as a value under a single entry, with a nested structure if necessary.

In some embodiments (see infra FIG. 2), if the robot has no network connection and is instead working with removable media devices (e.g., USB drive), the sync algorithm operates in the same way as in the network-connected case. Unlike having a client device talk over the network in discrete requests, a protocol may be designed for online traffic that aims to explicitly enable the removable media case. In the removable media case, an admin user downloads an update package from the Web Portal that contains everything that the robot needs to know about all users and cases; when given the update package, it processes it, and writes a response; then the admin user uploads it to the Web Portal. In an alternative embodiment, the robot writes first, and the response is downloaded from the Web Portal. The connected sync protocol could operate in the same way—one download, and one upload, rather than send traffic back and forth. In one embodiment a smart device (e.g., not a "dumb" removable media device) may be used that serves up the same protocol as the Web Portal, but which is presented to the robot in the same physical location. Using the Web Portal's protocol (which, in this embodiment, doesn't need to be constrained to one download and one upload; it can be a traditional protocol with lots of back-and-forth), the smart device does its syncing with the robot; then the admin user disconnects from the robot and connects to the Internet, where the smart device performs update functions with the Web Portal. The actual interaction with media may be assumed to be done by hospital IT administrators, not clinical staff members.

In one embodiment, the system features a watcher API, allowing apps across the system to monitor a given key for updates. This can be used to have multiple apps communicate with each other (e.g., an imagery viewer app can mirror the viewpoint of another instance of the app), or to serve as a means of notifying components of the system of changes in system state (e.g., a user has logged in, so the system should have its interface react accordingly).

Other advantages of the system disclosed herein relate to equipping the system according to surgeon preferences, per procedure type. The system may set general preferences, and also allow surgeons to make settings that are effective given a procedure type; then, when the case type is set during case planning, the system can configure the robot appropriately for that case type. For example, a particular surgeon may indicate that for a partial nephrectomy, there is a preference to always have the ICG (indocyanine green, a dye used in making anatomy clear for some surgeries) application open; then, when that particular surgeon is scheduled for a case, the system would have the ICG app either open or closed depending on the previously-set case type.

Advantages of the instant disclosure include identical worldwide user experience, and automatic sync of systems, with no clinical staff member involvement. The latest modification to user preferences may be the one applied, even if a robot with an older version of a preference value is the last to sync. Thus, conflicts are resolved efficiently and without problems to the user. Bandwidth usage is also minimized, and consequently the system syncs at high speed. Moreover, the robot is configured per case type, per user, which is highly advantageous to streamline surgical procedures.

The following disclosure discusses the embodiments mentioned above, as well as other embodiments, as they relate to the figures.

FIG. 1A illustrates a system 100A for global synchronization of surgical robots, in accordance with an embodiment of the disclosure. System 100A includes first surgical robotic system 101A (including user interface 103A and surgical robot 105A), second surgical robotic system 101B (including user interface 103B and surgical robot 105B), network 107, servers 109 (including storage and processing capabilities), personal computer 111, smartphone 113, speaker system 115, and hospital scheduler 117. It is appreciated that all of the components depicted can communicate and send data (including user preferences) to one another via network 107 (e.g., the internet, a local area network, or the like).

As shown, surgical robotic systems 101A and 101B include user interface 103A/103B coupled to receive user input (e.g., through the joystick, buttons, and pedals depicted), and a communication system (e.g., wired or wireless network connection, USB port, CD ROM drive/port, or the like) coupled to communicate with one or more external devices (e.g., network 107, servers 109, personal computer 111, smartphone 113, speaker system 115, hospital scheduler 117, or the like). The devices depicted may include first user preferences (e.g., user preferences saved remotely to the cloud or the like such as starting arm position for surgical robot 105A, seat height for user interface 103A, or the like). The surgical robotic systems 101A/101B also include memory (disposed within the robots), and the memory includes a database (see, e.g., FIG. 1B database 129) storing second user preferences (e.g., user preferences saved locally in the robot such as starting arm position for surgical robot 105A, seat height for user interface 103A, or the like). A controller (e.g., general purpose processor(s), application specific integrated circuits, or the like) in the surgical robotic systems 101A/101B is coupled to the user interface 103A/103B, the communication system, and the memory in surgical robotic systems 101A/101B. The controller includes logic that when executed by the controller causes the surgical robotic system 101A/101B to perform operations. The operations may include: receiving user input from the user interface 103A/103B; in response to receiving the user input, retrieving the first user preferences using the communication system (e.g., retrieving the first user preferences from the cloud or other remote device like those depicted); and in response to receiving the user input, retrieving the second user preferences from the database (e.g., retrieving the second user preferences from local memory in the robot). The controller may then resolve conflicts between the first (remote) user preferences and the second (local) user preferences to create a revised set of user preferences. The revised set of user preferences may include preferences from at least one of the first user preferences or the second user preferences. For example, all of the first (remote) user preferences may be used, all of the second (local) user preferences may be used, or a combination of the two may be used, to form the revised set of user preferences after conflicts (if any) are resolved. As will be discussed in greater detail later, other sources of user preferences may also be used to form the revised set of user preferences, in accordance with the teachings of the present disclosure. Then, once the revised set of user preferences is formed, the revised set of user preferences may be applied to the surgical robotic system (e.g., surgical robot 105A/105B arm height may be adjusted, control settings may be adapted, or the like).

In some embodiments, the first user preferences and the second user preferences include one or more timestamps (e.g., the surgical robot 103A default arm height was set on Apr. 1, 2018 at 10:43 am), and conflicts are resolved by using the user preferences with the most recent timestamp. For example, a default surgical robot arm height could have been set in the first (remote) user preferences on Apr. 1, 2018 at 10:43 am, and a default surgical robot arm height could have been set in the second (local) user preferences on Apr. 1, 2018 at 10:50 am. In this case, the arm height in the second user preferences would be applied because it was updated most recently.

In some embodiments, a clock (e.g., clock in the processor, quartz timekeeper, or the like) is coupled to, or included in, the controller, and the controller may synchronize the clock with a central time authority using the communication system. For example the central time authority may be on network 107, and surgical robotic systems 101A/101B may periodically synchronize their internal clocks to the central time authority. This way, all user preferences input to the system are given an accurate timestamp. As described above, in some embodiments, the system 101A may receive new user preferences from user interface 103A/103B, apply a timestamp to the new user preferences using the clock, and store the new user preferences in a local database. In some embodiments, these new user preferences, and the timestamp associated with the new user preferences, may be sent to the one or more external devices (e.g., the cloud and any of the devices depicted in FIG. 1A) using the communication system in the surgical robotic systems 101A/101B. In one embodiment, user preferences associated with the clock may include date/time/timezone settings, auto adjustment for daylight savings, and frequency of sync with the central time authority and other data on the cloud.

In some embodiments, the robot preferences may be changed each time a new surgery is set to occur based on the order of surgeries in the hospital scheduler 117 (e.g., an application running on one or more servers 109 that is used to schedule room availability, staff, and the like). Similarly, the robot settings may be adjusted in advance of the surgeon arriving using an application running on laptop 111 or smartphone 113. The robot may automatically announce changes (to the hospital staff) to end time of surgeries or the like using microphone 115.

Figure 1B:
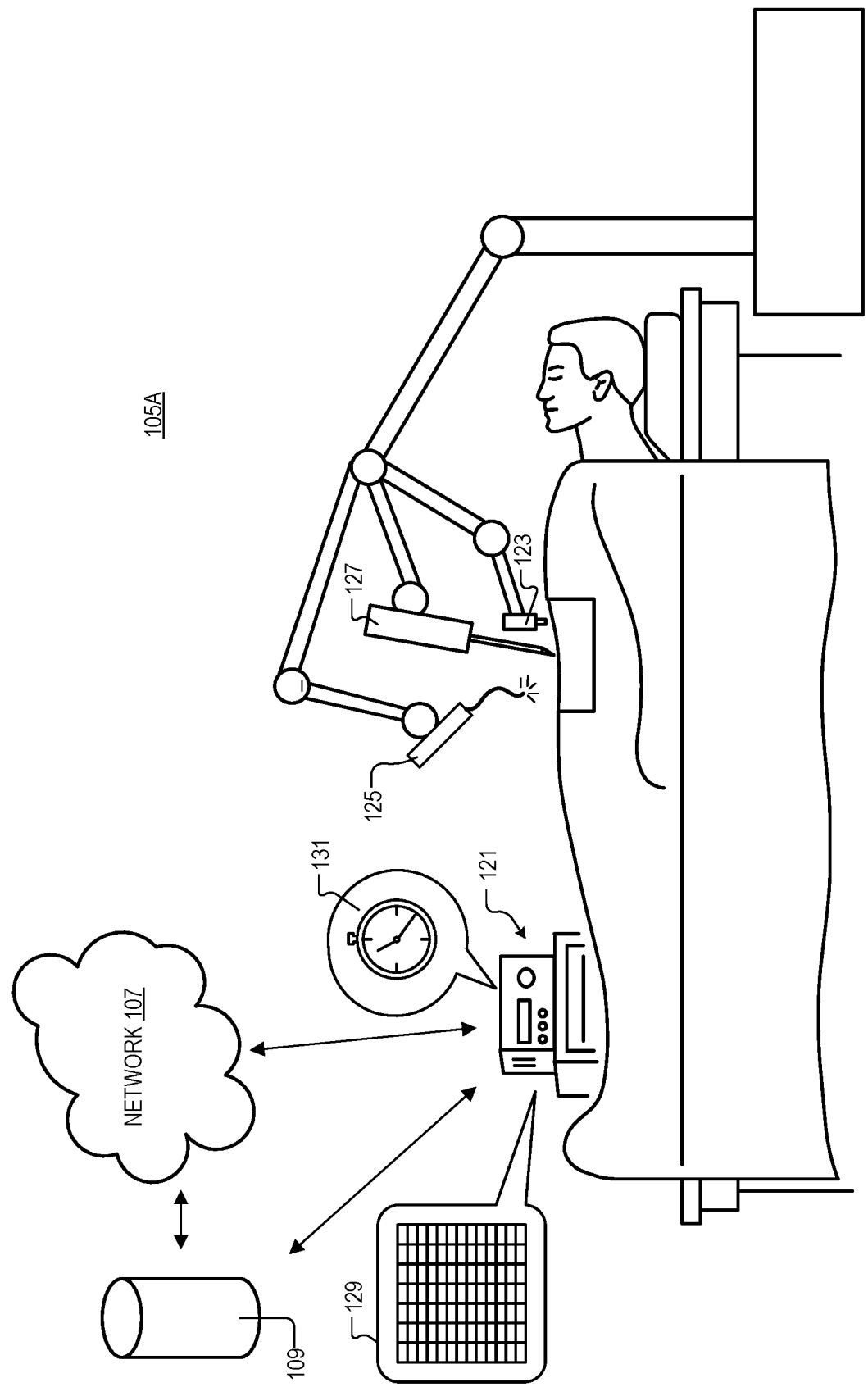
FIG. 1B illustrates a surgical robot which may be used in the system of FIG. 1A, in accordance with an embodiment of the disclosure.

FIG. 1B illustrates a surgical robot 105A which may be used in the system of FIG. 1A, in accordance with an embodiment of the disclosure. Surgical robot 105A includes camera 123, tool driver 127 (which can interchangeably accept any number of tools—stapler, hook, grasper, etc.—but here is holding a scalpel), endoscope 125 (with light source), controller 121 (including clock 131 and database 129), network 107 (e.g., the same network depicted in FIG. 1A), and storage 109 (e.g., hard disks or the like disposed in servers 109 from FIG. 1A). As shown, surgical robot 105A may be used to hold surgical instruments (e.g., each arm holds an instrument—or multiple instruments that are independently controlled—at the distal ends of the arm) and perform surgery, diagnose disease, take biopsies, or conduct any other procedure a doctor could perform. Surgical instruments may include scalpel 127, forceps, camera 123 (which may be in endoscope 125), endoscope 125, or the like. While surgical robot 105A only has three arms, one skilled in the art will appreciate that surgical robot 105A is merely a cartoon illustration, and that surgical robot 105A can take any number of shapes depending on the type of surgery needed to be performed and other requirements. Surgical robot 105A may be coupled to controller 121, network 107, and/or storage 109 either by wires or wirelessly. Furthermore, surgical robot 121 may be coupled (wirelessly or by wires) to a user interface (e.g., user interface system of FIG. 1C) to receive instructions from a surgeon or doctor, and send data (e.g., video) to a display. The user interface (UI), and user of the UI, may be located very close to the surgical robot 105A and patient (e.g., in the same room) or may be located many miles apart. Thus, surgical robot 105A may be used to perform surgery where a specialist is many miles away from the patient, and instructions from the surgeon are sent over the internet or secure network (e.g., network 107).

As shown, camera 121 is coupled to capture a video of a surgery performed by surgical robot 105A. Controller 121 is coupled to surgical robot 105A to control the motion of the one or more arms, control the one or more instruments, and receive the video from camera 123. In some embodiments, the first (remote) user preferences (which may be held in storage 109) or the second (local) user preferences (which may be stored on database 129) include at least one of default positioning information for the one or more instruments (e.g., where the one or more instruments will be positioned prior to surgery), or motion scaling settings for the one or more instruments (e.g., how sensitive the robot controls are—a lot of user interface device movement to produce a little instrument movement, or vice versa). In some embodiments, surgical robot 105A may restrict the movement of its one or more arms if an anomaly is detected (e.g. user dropping or fumbling a user input device) and the user preferences may determine the amount of motion restriction applied in this situation. For example, surgical robot 105A may slow the motion of the one or more arms, entirely stop movement of the one or more arms, or pause the movement of the one or more arms depending on the user's preferences.

In some embodiments, user preferences for endoscope 125 may include: illuminator (e.g., LEDs) in endoscope 125 on/off, illuminator power level, scope up/down, digital zoom level of image sensor in endoscope 125, color temperature of light output from endoscope, color temperature of images captured by the endoscope.

In one embodiment, camera 121 (e.g., including a CMOS image sensor or the like), pressure sensors (e.g., stress, strain, etc., disposed in the arms of robot 121), actuators (e.g., disposed in the arms of surgical robot 105A and including force measurement systems) and the like, are all used to control surgical robot 121 and ensure accurate motions and applications of pressure. Furthermore, these sensors may provide information to controller 121 which uses a feedback loop to continually adjust the location, force, etc., applied by surgical robot 105A. In some embodiments, sensors in the arms of surgical robot 105A may be used to determine the position of the arms relative to organs and other anatomical features. For example, surgical robot may store and record coordinates of the instruments at the end of the arms, and these coordinates may be used in conjunction with a video feed (or information derived from a soft tissue 3D simulator) to determine the location of the arms and anatomical features. It is appreciated that there are a number of different ways (e.g., from images, mechanically, time-of-flight laser systems, etc.) to calculate distances between components in system 105A and any of these may be used to determine surgical instrument location, in accordance with the teachings of the present disclosure.

Figure 1C:
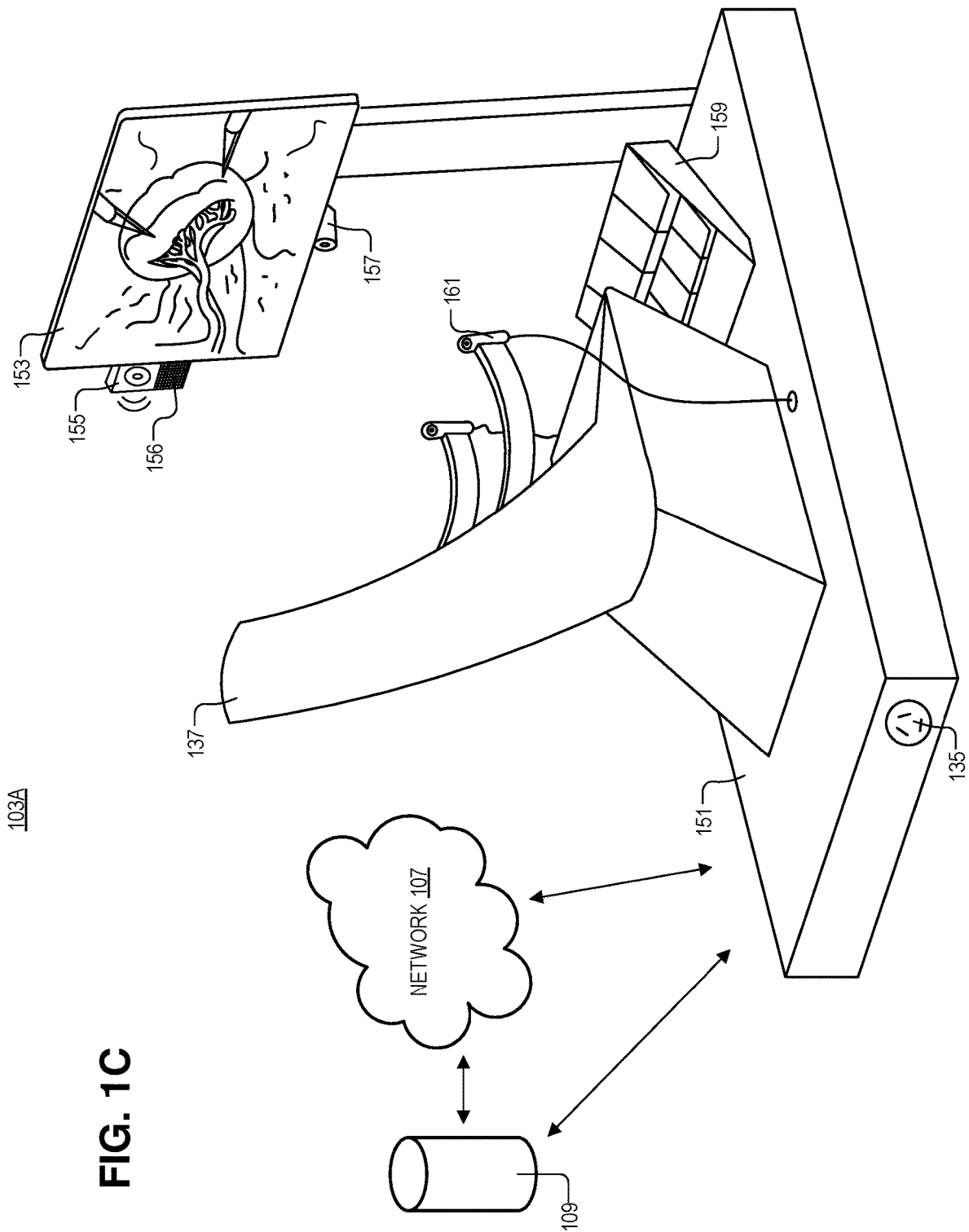
FIG. 1C illustrates a user interface system, which may be used with the surgical robot in FIG. 1B, in accordance with an embodiment of the disclosure.

FIG. 1C illustrates a user interface (UI) system 103A for use with the surgical robot in FIG. 1B, in accordance with an embodiment of the disclosure. Illustrated are network 107 (from FIG. 1A), storage 109 (also from FIG. 1A), power supply 135, command chair 137, controller 151 (e.g., processor disposed in the platform), display 153, speaker 155, microphone 156, camera 157, control pedals 159, and one or more user interface devices (UIDs) 161.

As shown, one or more UIDs 161 are shaped to be hand held. The surgeon may sit in command chair 137 while performing surgery. As illustrated, much of the UI system 100 may be included in a single assembled device (e.g., chair 137, controller 151, display 153, which all may be supplied power though power supply 135). One or more UIDs 161 may be detached from the arms of command chair 137, and once detached, UIDs 161 are configured to move freely in three dimensions since, in the depicted embodiment, they are only attached to a flexible cord. Accordingly, in some embodiments, UIDs 161 have six degrees of freedom (e.g., UID 161 is free to move its position backward/forward, down/up, right/left (translation in three perpendicular directions) combined with rotational movement around three perpendicular axes, normal axis (yaw), lateral axis (pitch), and longitudinal axis (roll)).

In some embodiments, user preferences for UIDs 161 may include: motion scaling settings, UID-to-robot-arm correspondence settings (which UID corresponds to which arm), or the like. Similarly, in some embodiments, user preferences for the display 153 may include: display 153 brightness, display 153 contrast, display 153 language, or the like. In one embodiment, camera 157 may be used as an eye tracker, and eye tracking settings (e.g., eye tracking functionality on/off) may be applied. In some embodiments, user interface 103A may be coupled to a hospital scheduler (e.g., hospital scheduler 117 from FIG. 1A) and user preferences may include turning on/off automatic updates (e.g., surgery end time, what step of the surgery is being performed, or the like) to the hospital scheduler.

In some embodiments, user preferences may include preferences for how UI system 103A is physically configured. For example, user preferences may include adjusting a height of seat/chair 137, adjusting a chair base tilt, adjusting armrest height of chair 137, adjusting an amount of reclining of chair 137, adjusting a distance from chair 137 to a display 153, adjusting a display 153 height relative to chair 137, adjusting a height/tilt of control pedals 159, adjusting a volume of speaker 155, or the like.

UI system 103A may run a variety of applications, and graphical representations of the applications may be present on display 153, these applications may be tiled and placed in a specific order based on how the user of the system has configured the graphical interface (which is one example of a GUI user preference). Similarly, user preferences may include volume and language settings for sounds emitted from speaker 156.

In some embodiments, user input (e.g., from UIDs 161) includes information indicating a type of surgery to be performed (e.g., gastric bypass, hysterectomy, prostatectomy, or cholecystectomy), and the first user preferences and the second user preferences include the user preferences for the type of surgery to be performed (e.g., the preferences the surgeon has when performing a gastric bypass). Accordingly, the revised set of user preferences applied to the surgical robotic system are for the type of surgery to be performed (e.g., the system applies the settings that are applicable for a gastric bypass).

Figure 2:
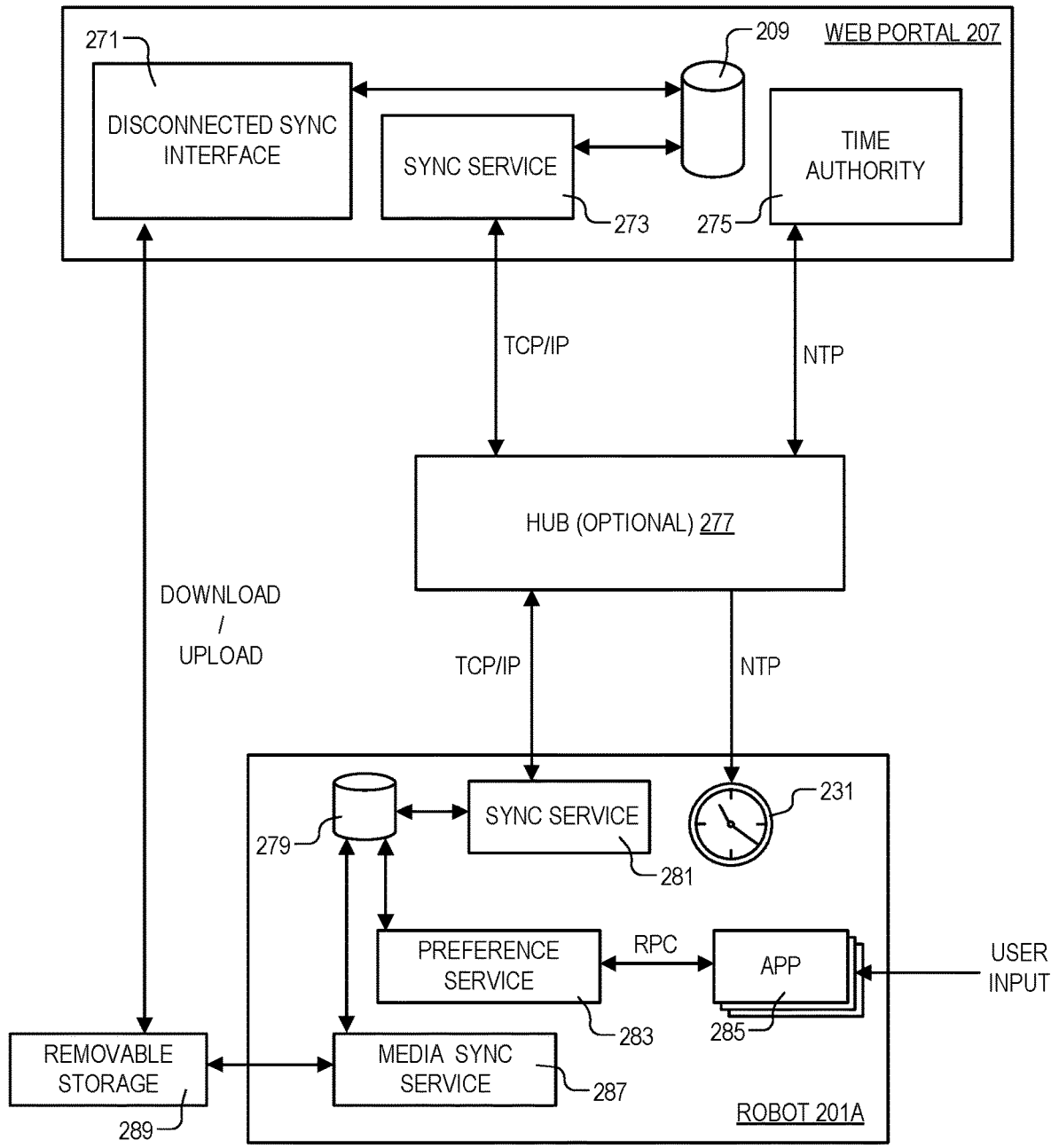
FIG. 2 illustrates a block diagram of a global synchronization architecture, in accordance with an embodiment of the disclosure.

FIG. 2 illustrates a block diagram of a global synchronization architecture, in accordance with an embodiment of the disclosure. Depicted is web portal 207 (which may be included in network 107 in FIG. 1A) that includes storage 209 (which may be included on servers 109 in FIG. 1A), disconnected synchronization interface 271, synchronization service 273, and a central time authority 275. In the depicted example (remote) storage 209, which may include user preferences, is coupled to both synchronization service 273 and disconnected synchronization interface 271 to send and receive data to surgical robotic system 201A.

Also depicted is surgical robotic system 201A (which may correspond to the surgical robotic system 101A in FIG. 1A) that includes clock 231, local storage 279, synchronization service 281, preference service 283, applications 285, and media synchronization service 287. Hub 277 is optionally coupled between web portal 207 and surgical robotic system 201A.

In the absence of a connection to web portal 207, removable storage device 289 (e.g., a flash drive, CD ROM, or the like) may be used to communicate data and user preferences between web portal 209 and surgical robotic system 201A by interfacing with media synchronization service 287 and disconnected synchronization interface 271. However, generally, data and user preferences may be shared between web portal 209 and surgical robotic system 201A by sending them directly through the internet or other network (e.g., using transmission control protocol (TCP)/internet protocol (IP)). Synchronization service 281 may send/receive data and user preferences from web portal 207. Local storage 279 may store data and user preferences locally on robot 201A. User preferences may be received from the user, by the user interface, with applications 285, and preference service 283 may send this data to local storage 279. As discussed above, clock 231 may be coupled to receive an accurate time reading from central time authority 275 (e.g., using a network time protocol (NTP)).

Figure 3:
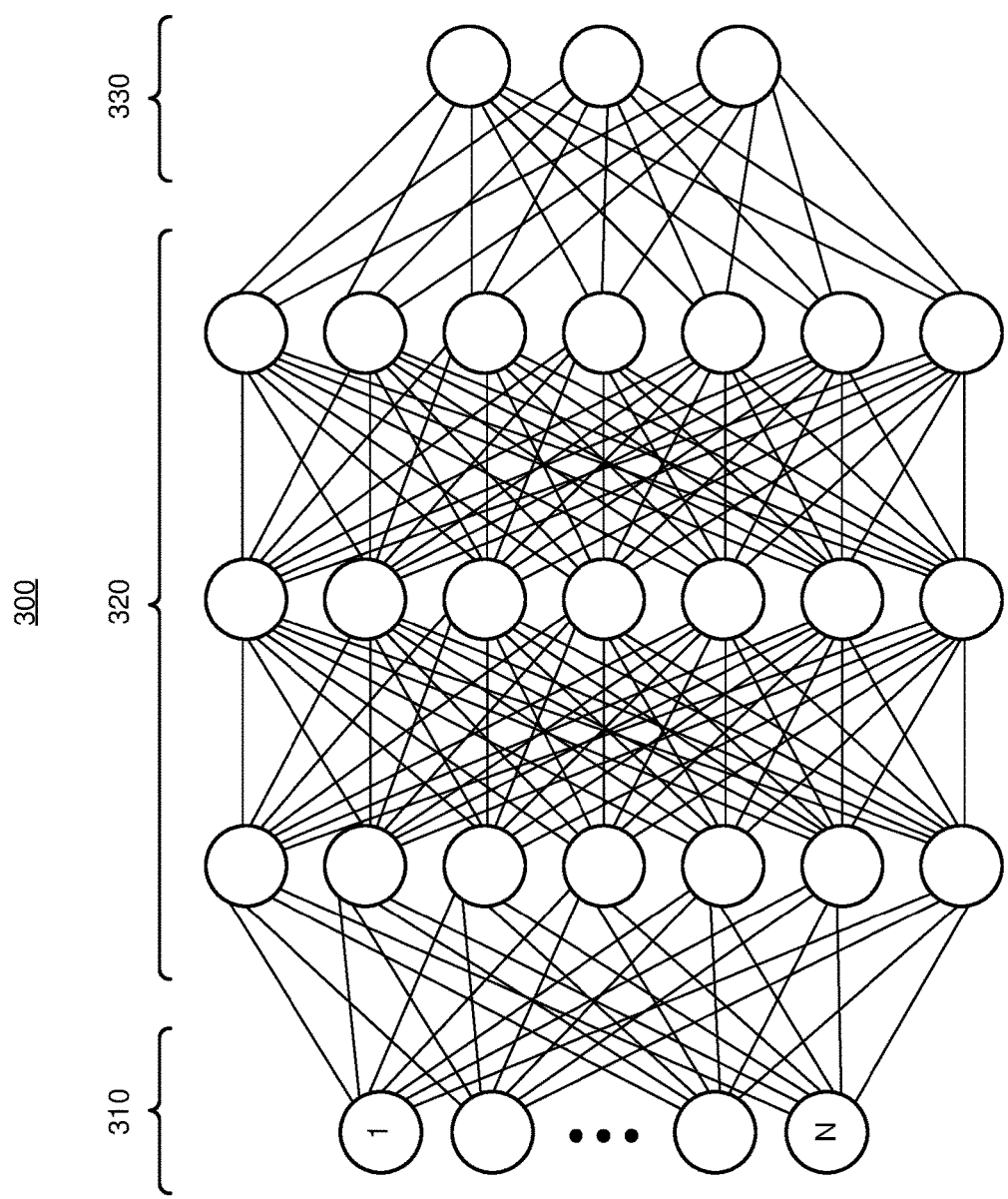
FIG. 3 is a graphical depiction of processes that may run on the system of FIG. 1A, in accordance with an embodiment of the disclosure.

FIG. 3 is a graphical depiction of machine learning algorithm 300 that may run on the e system of FIG. 1A, in accordance with an embodiment of the disclosure. Machine learning algorithm 300 includes an input layer 310, an output layer 330, and multiple hidden layers 320 disposed between the input layer 310 and the output layer 330. The number of nodes in input layer 310 may be dependent on the inputs (e.g., biometric information including user height, user weight, user age, user disabilities, user vision limitations, or the like), and output layer 330 may output at least some of the revised set of user preferences for the surgical robot using the biometric information. In some embodiments, the number of input nodes is related to the number of various inputs and their particular resolution (e.g., the amount of biometric information input into the system for a given user). It is appreciated that multiple machine learning algorithms like the one depicted may be running (and trained) separately for each input (e.g., one for each type of biometric information). The weight distribution for the connections between nodes is not illustrated, but it is appreciated that the specific values are highly dependent on the training or pre-training method, the number of training iterations (e.g., number of training samples) performed, to name a few.

The type of neural network utilized for the machine learning algorithm 300 is highly configurable and dependent on the inputs and the data being analyzed. Thus, in some embodiments, the machine learning model 300 may utilize radial basis function neural network, a recurrent neural network, long-short term memory network, a convolution neural network, a modular neural network, or other types of neural networks. As described above, machine learning algorithm 300 may be used in conjunction (e.g., at the same time or in some sequential order) with other algorithms to generate the revised set of user preferences, in accordance with the teachings of the present disclosure.

Figure 4:
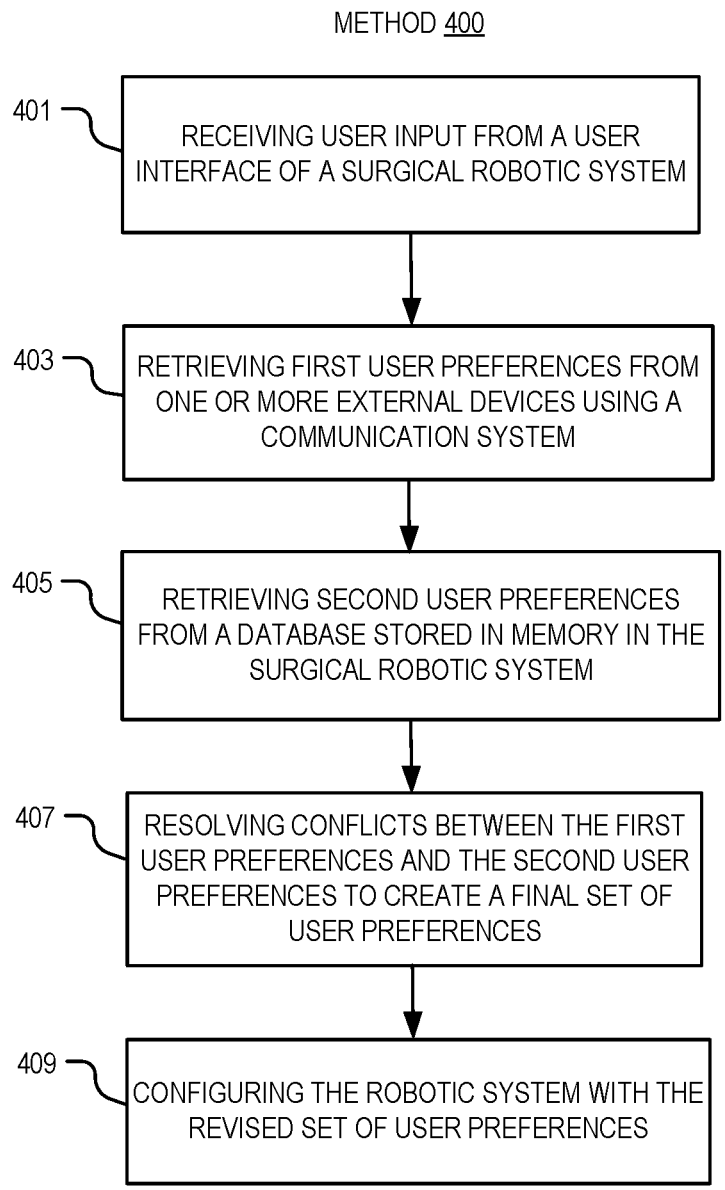
FIG. 4 illustrates a method of operating a surgical robotic system, in accordance with an embodiment of the disclosure.

FIG. 4 illustrates a method 400 of operating a surgical robotic system, in accordance with an embodiment of the disclosure. One of ordinary skill in the art having the benefit of the present disclosure will appreciate that the order of blocks (401-409) in method 400 may occur in any order or even in parallel. Moreover, blocks may be added to, or removed from, method 400 in accordance with the teachings of the present disclosure.

Block 401 shows receiving, with a controller, user input from a user interface of the surgical robotic system. In some embodiments, the user input may include user login information (e.g., username and password) and/or information indicating a type of surgery to be performed (e.g., a drop-down box on the UI that lets the user select a surgical procedure or class of tool settings). In some embodiments, the user input includes biometric information about the user, and the biometric information may include things like user height, user weight, user age, user disabilities, or user vision limitations.

Block 403 illustrates, in response to receiving the user input, retrieving first user preferences from one or more external devices (e.g., the cloud or remote servers) using a communication system. For example, the communication system may call the first user preferences from a database on the cloud or the like.

Block 405 describes, in response to receiving the user input, retrieving second user preferences from a database stored in local memory on the surgical robotic system.

Block 407 shows resolving, using the controller, conflicts between the first user preferences and the second user preferences to create a revised set of user preferences. This revised set of user preferences includes user preferences from at least one of the first set of user preferences or the second set of user preferences. In some embodiments, the first user preferences and the second user preferences include one or more timestamps, and conflicts are resolved by using the user preferences with the most recent timestamp. Put another way, in some embodiments, the surgical system may select only the most recently updated user preferences and apply them to the surgical system. For example, if there are two separate settings for the height of the user's chair, the most recently updated height will be selected.

In some embodiments, metrics other than time are used to resolve conflicts. For example, the user may have "master" preferences uploaded to the cloud that control in the event of a conflict on an individual system. Additionally, location of the surgery and surgical robot (which may be identified by a robot identifier number) being used may be used to resolve conflicts (e.g., only a particular type of surgery may be performed on a particular robot, so only preferences for that type of surgery are applied).

Block 409 illustrates applying the revised set of user preferences to the surgical robotic system. In some embodiments, this may include moving one or more arms of the surgical robotic system to a location based on the first user preferences or the second user preferences. In another or the same embodiment, applying the revised set of user preferences to the surgical robotic system may include user preferences for a specific type of surgery to be performed. For example, the user may have entered into the UI that a tonsillectomy will be performed; accordingly the system only applies user preferences applicable to performing a tonsillectomy, or the specific preferences that the user has recorded to be used when a tonsillectomy is being performed.

In embodiments where biometric information has been entered, a machine-learning algorithm may be used to generate at least some of the revised set of user preferences using the biometric information. For example, the system may adjust seat height, and UID positioning based on the user's height and/or arm length.

In some embodiments, simply entering unique login information (e.g., user ID and password), will result in the system applying the revised set of user preferences without any additional information. For example, a user profile may be saved to the database in the robotic system or in the cloud, and simply logging on will cause the robot to adapt all of the user's preferences.

In some embodiments, the user interface may receive new user preferences from the user, and apply a timestamp to the new user preferences using the clock. The user preferences may then be stored locally on the database in the robot. When an internet or other connection becomes available, the new user preferences, and the timestamp associated with the new user preferences, may be sent to one or more external devices using the communication system (e.g., via direct connection or removable storage medium).

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise. Processes may also occur locally or across distributed systems (e.g., multiple servers, processors, and memory). Machine learning algorithm architectures may be implemented in software or hardware.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A robotic system, comprising:
   a communication system adapted to communicate with one or more external devices that include first user preferences;
   memory storing a database including second user preferences; and
   a controller coupled to the communication system and the memory, wherein the controller includes logic that when executed by the controller causes the robotic system to perform operations, including:
      receiving user input from a user interface of the robotic system, wherein the user input includes biometric information about the user;
      in response to receiving the user input, retrieving the first user preferences using the communication system;
      in response to receiving the user input, retrieving the second user preferences from the database;
      resolving conflicts between the first user preferences and the second user preferences to create a revised set of user preferences including user preferences from at least one of the first user preferences or the second user preferences; and
      configuring the robotic system with the revised set of user preferences,
      wherein one or more entries in the first user preferences and the second user preferences are associated with corresponding existence flags that indicate whether associated entries either exist or have been deleted,
   wherein the logic includes a machine-learning algorithm, and wherein the machine-learning algorithm generates at least some of the revised set of user preferences to generate default preferences for configuring a surgical robot of the robotic system using the biometric information of the user.

2. The robotic system of claim 1, wherein the first user preferences and the second user preferences include one or more timestamps, and wherein conflicts are resolved by using the user preferences with a most recent timestamp.

3. The robotic system of claim 1, further comprising a clock coupled to the controller, wherein the controller further includes logic that when executed by the controller causes the robotic system to perform operations, including:
   synchronizing the clock with a central time authority using the communication system.

4. The robotic system of claim 3, wherein the controller further includes logic that when executed by the controller causes the robotic system to perform operations, including:
   receiving new user preferences with the user interface of the robotic system;
   applying a timestamp to the new user preferences using the clock; and
   storing the new user preferences in the database.

5. The robotic system of claim 4, wherein controller further includes logic that when executed by the controller causes the robotic system to perform operations, including:
   sending the new user preferences and the timestamp associated with the new user preferences to the one or more external devices using the communication system.

6. The robotic system of claim 1, further comprising one or more arms configured to hold one or more surgical instruments, and wherein the first user preferences or the second user preferences include at least one of default positioning information for the one or more surgical instruments, or motion scaling settings for the one or more instruments.

7. The robotic system of claim 1, wherein the user input includes information indicating a type of surgery to be performed, and wherein the first user preferences and the second user preferences are keyed to the type of surgery to be performed and configure the robotic system for the type of surgery to be performed.

8. The robotic system of claim 1, wherein the biometric information includes at least one of user height, user weight, user age, user disabilities, or user vision limitations.

9. The robotic system of claim 1, wherein the user input includes login information, and applying the revised set of user preferences occurs in response to the robotic system receiving the login information.

10. The robotic system of claim 1, wherein the communication system includes a port configured to receive a device containing a second memory, and wherein retrieving the first user preferences using the communication system includes receiving the first user preferences via the port and the first user preferences are stored on the second memory.

11. A method of operating a robotic system, comprising:
    receiving, with a controller, user input from a user interface of the robotic system;
    in response to receiving the user input, retrieving first user preferences from one or more external devices using a communication system;
    in response to receiving the user input, retrieving second user preferences from a database stored in memory in the robotic system;
    resolving, using the controller, conflicts between the first user preferences and the second user preferences to create a revised set of user preferences, including user preferences from at least one of the first set of user preferences or the second set of user preferences; and
    configuring the robotic system with the revised set of user preferences,
    wherein one or more entries in the first user preferences and the second user preferences are associated with corresponding existence flags that indicate whether associated entries either exist or have been deleted,
    wherein the user input includes biometric information about the user, and wherein a machine-learning algorithm generates at least some of the revised set of user preferences using the biometric information.

12. The method of claim 11, wherein the first user preferences and the second user preferences include one or more timestamps, and wherein conflicts are resolved by using the user preferences with a most recent timestamp.

13. The method of claim 11, further comprising synchronizing a clock disposed in the robotic system with a central time authority using the communication system.

14. The method of claim 13, further comprising:
receiving new user preferences with the user interface;
applying a timestamp to the new user preferences using the clock; and
storing the new user preferences in the database.

15. The method of claim 14, further comprising sending the new user preferences and the timestamp associated with the new user preferences to the one or more external devices using the communication system.

16. The method of claim 11, wherein applying the revised set of user preferences to the robotic system includes moving one or more arms of the robotic system to a location based on the first user preferences or the second user preferences.

17. The method of claim 11, wherein the user input includes information indicating a type of surgery to be performed, and wherein the first user preferences and the second user preferences include the user preferences for the type of surgery to be performed, and wherein applying the revised set of user preferences to the robotic system includes the user preferences for the type of surgery to be performed.

18. The method of claim 17, wherein the biometric information includes at least one of user height, user weight, user age, user disabilities, or user vision limitations.

19. The method of claim 11, wherein the user interface includes a seat, and wherein applying the revised set of user preferences includes at least one of adjusting a height of the seat, adjusting armrest height of the seat, adjusting an amount of reclining of the seat, adjusting a distance from the seat to a display included in the user interface.

20. The method of claim 11, wherein receiving the user input includes receiving login information, and wherein applying the revised set of user preferences occurs in response to the robotic system receiving the login information.

21. A method of operating a robotic system, comprising:
receiving, with a controller, user input from a user interface of the robotic system;
in response to receiving the user input, retrieving first user preferences from one or more external devices using a communication system;
in response to receiving the user input, retrieving second user preferences from a database stored in memory in the robotic system;
resolving, using the controller, conflicts between the first user preferences and the second user preferences to create a revised set of user preferences, including user preferences from at least one of the first set of user preferences or the second set of user preferences; and
configuring the robotic system with the revised set of user preferences,
wherein the user input includes biometric information about the user, and wherein a machine-learning algorithm generates at least some of the revised set of user preferences using the biometric information.

22. A machine readable medium storing instructions that, when executed by a controller, cause the controller to perform operation including:
receiving user input from a user interface of a robotic system;
in response to receiving the user input, retrieving first user preferences from one or more external devices using a communication system;
in response to receiving the user input, retrieving second user preferences from a database stored in memory of the robotic system;
resolving conflicts between the first user preferences and the second user preferences to create a revised set of user preferences, including user preferences from at least one of the first set of user preferences or the second set of user preferences; and
configuring the robotic system with the revised set of user preferences,
wherein the user input includes biometric information about the user, and wherein a machine-learning algorithm generates at least some of the revised set of user preferences using the biometric information.

* * * * *